US009872960B2

(12) United States Patent
Tran et al.

(10) Patent No.: US 9,872,960 B2
(45) Date of Patent: Jan. 23, 2018

(54) DOSE DIVIDER SYRINGE

(71) Applicant: Teleflex Medical Incorporated, Research Triangle Park, NC (US)

(72) Inventors: Huy Tran, Riverton, UT (US); Perry Croll, Sandy, UT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 455 days.

(21) Appl. No.: 14/563,106

(22) Filed: Dec. 8, 2014

(65) Prior Publication Data
US 2016/0022916 A1 Jan. 28, 2016

Related U.S. Application Data

(60) Provisional application No. 62/028,385, filed on Jul. 24, 2014.

(51) Int. Cl.
*A61M 5/315* (2006.01)
(52) U.S. Cl.
CPC .... *A61M 5/31511* (2013.01); *A61M 5/31595* (2013.01)
(58) Field of Classification Search
CPC .......... A61M 5/31595; A61M 5/31526; A61M 5/3156; A61M 5/31511
USPC ................................................ 604/210, 229
See application file for complete search history.

(56) References Cited

U.S. PATENT DOCUMENTS

| 3,045,673 | A | | 7/1962 | Hein |
| 4,659,327 | A | | 4/1987 | Bennett et al. |
| 4,840,616 | A | | 6/1989 | Banks |
| 5,009,645 | A | | 4/1991 | Silver et al. |
| 5,104,380 | A | | 4/1992 | Holman et al. |
| 5,205,825 | A | * | 4/1993 | Allison ............... A61M 5/5013 604/110 |
| 5,232,459 | A | | 8/1993 | Hjertman |
| 5,300,041 | A | | 4/1994 | Haber et al. |

(Continued)

FOREIGN PATENT DOCUMENTS

| WO | 9907421 A1 | 2/1999 |
| WO | 2008057976 A2 | 5/2008 |

OTHER PUBLICATIONS

International Search Report (ISR) (PCT Form PCT/ISA/210) and the Written opinion of the International Searching Authority of International Application No. PCT/US2014/069065, dated Mar. 17, 2015.

*Primary Examiner* — Phillip Gray
(74) *Attorney, Agent, or Firm* — Baker & Hostetler LLP

(57) ABSTRACT

A syringe includes a barrel having an internal surface defining an internal bore therein, and a plunger disposed within the internal bore of the barrel. A distal end of the plunger is inserted into a proximal end of the barrel. At least one radial projection is disposed on an external surface of the plunger, the at least one radial projection includes a proximal ramp and a distal ramp. The distal ramp includes a first point being a point of incipient contact with the internal surface of the barrel, and the at least one radial projection has a first slope relative to the longitudinal axis at the first point. The at least one radial projection has a second slope at a second point along the proximal ramp. An absolute value of the first slope is different from an absolute value of the second slope.

14 Claims, 5 Drawing Sheets

(56) References Cited

U.S. PATENT DOCUMENTS

| | | |
|---|---|---|
| 5,318,544 A | 6/1994 | Drypen et al. |
| 5,328,486 A | 7/1994 | Woodruff |
| 5,599,314 A | 2/1997 | Neill |
| 5,601,077 A | 2/1997 | Imbert |
| 5,938,642 A | 8/1999 | Burroughs et al. |
| 5,951,526 A | 9/1999 | Korisch et al. |
| 5,975,355 A | 11/1999 | Cecala et al. |
| 5,988,452 A | 11/1999 | Dent et al. |
| 6,419,656 B1 | 7/2002 | Vetter et al. |
| 6,562,007 B1 | 5/2003 | Falsey |
| 6,579,269 B1 | 6/2003 | Kleyman |
| 6,972,006 B2 | 12/2005 | Ferguson |
| 7,470,259 B2 | 12/2008 | Hoyle, Jr. |
| 7,901,384 B2 | 3/2011 | Kleyman et al. |
| 8,216,193 B2 | 7/2012 | Rolla |
| 2003/0004467 A1 | 1/2003 | Musick et al. |
| 2005/0137532 A1 | 6/2005 | Rolla |
| 2009/0287161 A1 | 11/2009 | Traub et al. |
| 2011/0118701 A1 | 5/2011 | Baney et al. |
| 2011/0313397 A1 | 12/2011 | Gold |
| 2013/0090603 A1 | 4/2013 | Hoyle, Jr. |

\* cited by examiner

DOSE DIVIDER SYRINGE

CROSS-REFERENCE TO RELATED APPLICATIONS

This application claims priority to U.S. Provisional Patent Application No. 62/028,385, entitled "Dose Divider Syringe," filed on Jul. 24, 2014, the disclosure of which is hereby incorporated by reference in its entirety.

TECHNICAL FIELD

This patent disclosure relates generally to syringes and, more particularly to syringes that provide tactile feedback of a dose quantity delivered.

BACKGROUND

Syringes are known for storing and transporting substances with fluid properties such as gases, liquids, pastes, slurries, and the like. A syringe may include a barrel defining a bore in communication with a port, and a piston disposed within the barrel. Translation of the piston away from the port may draw material into the barrel through the port. Alternatively, translation of the piston toward the port may expel material out of the barrel through the port.

A syringe barrel may be formed from a transparent or translucent material, such that a position of the piston within the bore is visible through the barrel. Further, the syringe barrel may include indicia disposed thereon, such that longitudinal alignment of the piston relative to the indicia may visually indicate a volume of material stored between the piston and the port.

U.S. Pat. No. 5,009,645 (hereinafter, "the '645 patent") purports to describe a syringe for dispensing measured quantities of a material (e.g., a medicament). The syringe from the '645 patent includes a barrel, a plunger rod having a cruciform transverse cross section, and an infinitely adjustable stop member secured to the plunger rod for positively setting the length of travel of the plunger rod to thereby control the volume of material dispensed from the syringe. However, sequential delivery of multiple doses using the syringe from the '645 patent may be subject to dosage errors resulting from inaccurate displacement of the infinitely adjustable stop member between dose deliveries, undue time consumption to adjust the position of the infinitely adjustable stop member, or both.

U.S. Patent Publication No. 2005/0137532 (hereinafter, "the '532 publication") purports to describe a unit to administer medication having a plunger with non-reusable stroke stops sequentially arranged along the plunger. According to the '193 patent, the stroke stops are frangible about a weakening line, such that each broken stroke stop enables the forward movement of the impelling plunger and the administration of a corresponding dose. However, the stroke stops of the '532 publication may interfere with filling an empty syringe so configured, and therefore limit application to pre-filled syringes. Further, the stroke stops of the '532 patent are inherently non-reusable because of their frangible nature, and the stroke stops may be complex and expensive to manufacture.

U.S. Pat. No. 5,318,544 (hereinafter, "the '544 patent") purports to describe a syringe for metering predetermined volumes of fluid therefrom. The syringe of the '544 patent includes a tube, a clip, and a metering plunger having stop surfaces disposed thereon, where the plunger is inserted through an opening in the clip and is slidably located within the syringe tube. However, the plunger stop surfaces of the '544 patent have complex shapes that could be difficult or expensive to manufacture. Further, the stop surfaces of the '544 patent may interfere with filling an empty syringe by requiring rotation of the plunger in addition to axial translation during a filling step.

U.S. Pat. No. 6,579,269 (hereinafter, "the '269 patent") purports to describe a syringe with a structure that allows variation in sliding displacement of the plunger which may be accompanied by an audible sound. U.S. Patent Application Publication No. 2009/0287161 (hereinafter, "the '161 publication") purports to describe a syringe including physical stops or dosage administered indicators which can act to prevent hydraulic momentum from continuing to deliver fluid after thumb pressure is lifted off of the push rod. However, neither the '269 patent nor the '161 publication provides asymmetric ramps for tailoring differences in deceleration and acceleration resistance forces for movement of a plunger within a dose dividing syringe.

Accordingly, there is a need for apparatus and methods to address the above-identified shortcomings of conventional syringes, as well as other shortcomings in the art.

SUMMARY

According to an aspect of the disclosure, a syringe comprises a barrel having an internal surface defining an internal bore therein, and a plunger disposed within the internal bore of the barrel. A distal end of the plunger is inserted into a proximal end of the barrel, and a proximal end of the plunger is opposite the distal end of the plunger along a longitudinal axis of the plunger. At least one radial projection is disposed on an external surface of the plunger, the at least one radial projection includes a proximal ramp and a distal ramp, the proximal ramp being disposed on a proximal side of the at least one radial projection, and the distal ramp being disposed on a distal side of the at least one radial projection. The distal ramp includes a first point being a point of incipient contact with the internal surface of the barrel, the first point being located at a first radial distance from the longitudinal axis, and the at least one radial projection having a first slope relative to the longitudinal axis at the first point. The at least one radial projection has a second slope at a second point along the proximal ramp located a second radial distance from the longitudinal axis, the second radial distance being substantially equal to the first radial distance. An absolute value of the first slope is different from an absolute value of the second slope.

According to another aspect of the disclosure, a plunger for a syringe comprises a shaft extending along a longitudinal axis of the plunger; a piston disposed at a proximal end of the plunger, the piston configured to engage an internal bore of the syringe in sliding and sealing engagement, a distal end of the plunger being opposite the proximal end of the plunger; and at least one radial projection disposed on an outer surface of the shaft. The at least one radial projection includes a proximal ramp and a distal ramp, the proximal ramp being disposed on a proximal side of the at least one radial projection, and the distal ramp being disposed on a distal side of the at least one radial projection. A linear portion of the proximal ramp has a proximal slope with respect to the longitudinal axis, and a linear portion of the distal ramp has a distal slope with respect to the longitudinal axis. An absolute value of the proximal slope is different from an absolute value of the distal slope.

According to another aspect of the disclosure, a plunger for a syringe comprises a shaft extending along a longitudinal axis of the plunger; a piston disposed at a proximal end of the plunger, the piston configured to engage an internal bore of the syringe in sliding and sealing engagement, a distal end of the plunger being opposite the proximal end of the plunger; and at least one radial projection disposed on an outer surface of the shaft. The at least one radial projection includes a proximal ramp and a distal ramp, the proximal ramp being disposed on a proximal side of the at least one radial projection, and the distal ramp being disposed on a distal side of the at least one radial projection. The distal ramp extends at least partly in a radial direction to a point of maximum distal ramp radial height, the radial direction being normal to the longitudinal axis, and the proximal ramp extending at least partly in the radial direction to a point of maximum proximal ramp radial height. The distal ramp is asymmetric with the proximal ramp about a plane normal to longitudinal axis and passing through a point halfway between the point of maximum proximal ramp radial height and the point of maximum distal radial height in an axial direction parallel to the longitudinal axis.

Another aspect of the disclosure provides a method for operating a syringe. The syringe includes a barrel having an internal surface defining an internal bore therein, a plunger disposed within the internal bore of the barrel, a distal end of the plunger being inserted into a proximal end of the barrel, a proximal end of the plunger being opposite the distal end of the plunger along a longitudinal axis of the plunger, and at least one radial projection disposed on an external surface of the plunger. The at least one radial projection includes a proximal ramp and a distal ramp, the proximal ramp being disposed on a proximal side of the at least one radial projection, and the distal ramp being disposed on a distal side of the at least one radial projection. The method comprises delivering a first dose of material from the syringe by translating the plunger relative to the barrel along the longitudinal axis of the plunger in a first direction until the proximal ramp of the plunger engages the internal surface of the barrel at a proximal point of incipient contact, the first direction extending from the proximal end of the plunger toward the distal end of the plunger; sensing an increase in translational resistance between the plunger and the barrel caused by contact between the proximal ramp and the internal surface of the barrel; ending the delivering of the first dose of material from the syringe based on the sensing the increase in translational resistance between the plunger and the barrel; and delivering a second dose of material from the syringe by translating the plunger relative to the barrel along the longitudinal axis of the plunger in the first direction through a distal point of incipient contact between the distal ramp of the plunger and the internal surface of the barrel, the at least one radial projection having a first slope relative to the longitudinal axis at the proximal point of incipient contact and a second slope relative to the longitudinal axis at the distal point of incipient contact, an absolute value of the first slope being different from the absolute value of the second slope.

DETAILED DESCRIPTION

Figure 1:
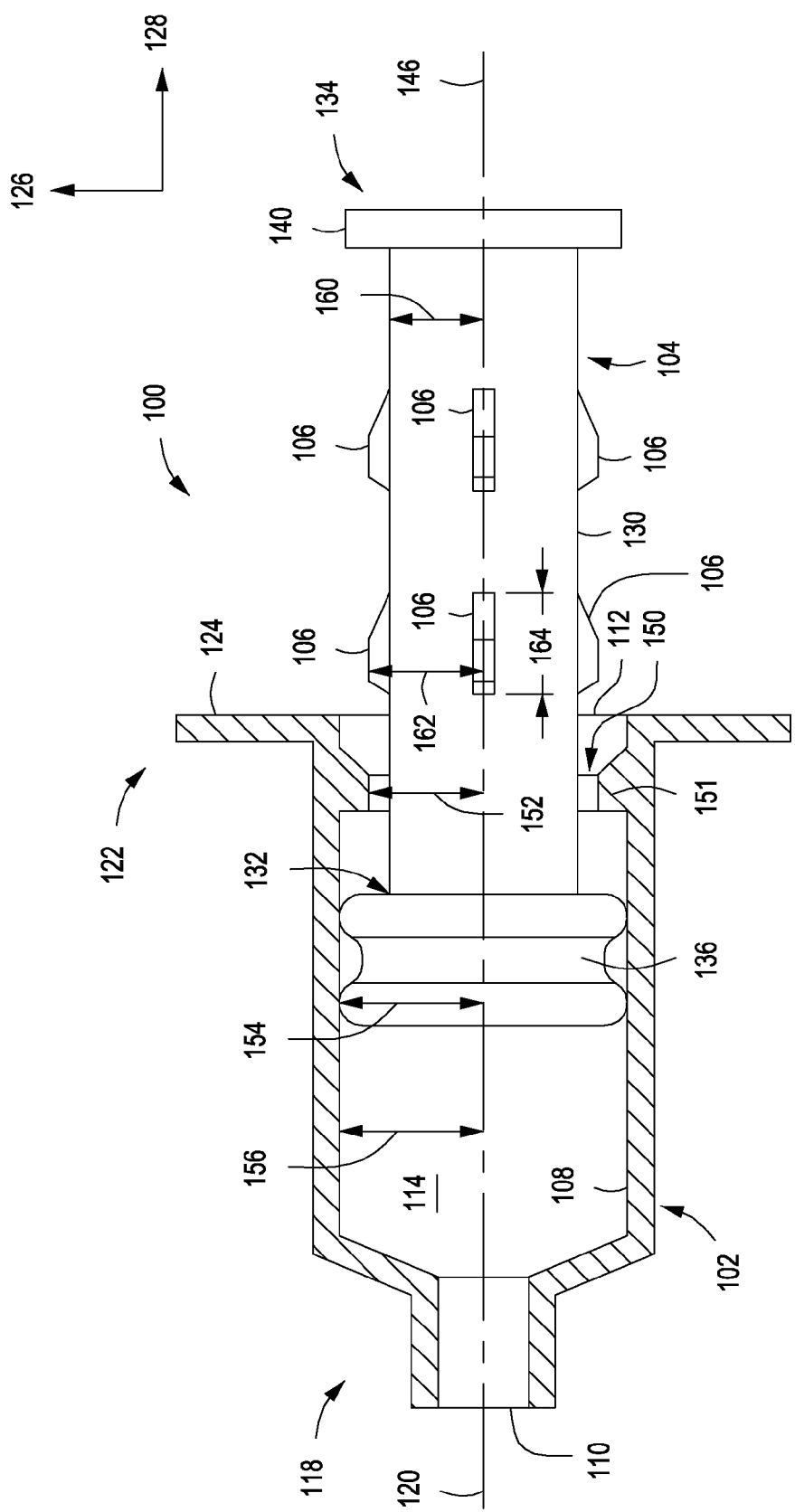
FIG. 1 is a schematic view of a syringe, according to an aspect of the disclosure.

Different aspects of the disclosure will now be described with reference to the drawing figures, in which like reference numerals refer to like parts throughout, unless otherwise specified.

FIG. 1 shows a schematic view of a syringe 100, according to an aspect of the disclosure. The syringe 100 includes a barrel 102, a plunger 104, and at least one radial projection 106 disposed on the plunger 104. The barrel 102 has an internal surface 108 defining a first aperture or port 110, a second aperture or port 112, and an internal bore 114 extending therebetween. The first aperture 110 may be located at a distal end 118 of the barrel 102 along a longitudinal axis 120 of the barrel 102, and the second aperture 112 may be located at a proximal end 122 of the barrel 102 along the longitudinal axis 120 of the barrel 102. It will be appreciated that the first aperture 110 may be centered on the longitudinal axis 120 but need not be centered on the longitudinal axis 120 to be considered located at the distal end 118 of the barrel 102. Further, it will be appreciated that the second aperture 112 may be centered on the longitudinal axis 120 but need not be centered on the longitudinal axis 120 to be considered located at the proximal end 122 of the barrel 102.

The barrel 102 may include a flange 124 extending away from the barrel 102 at least partly in a radial direction 126, where the radial direction 126 is perpendicular to an axial direction 128. According to an aspect of the disclosure, the axial direction 128 is parallel to the longitudinal axis 120. According to another aspect of the disclosure, the flange 124 extends away from the barrel 102 in substantially the radial direction 126.

The plunger 104 includes a shaft 130 having a distal end 132 and a proximal end 134. A piston 136 is coupled to the distal end 132 of the shaft 130, and a radial projection 106 extends from an outer surface of the shaft 130 at least partly in the radial direction 126. The radial projection is disposed along a longitudinal length of the shaft 130 between the distal end 132 and the proximal end 134 of the shaft. The plunger 104 may further include a flange 140 disposed at the proximal end 134 of the shaft 130, where the flange 140 extends outward from the shaft 130 at least partly in the radial direction 126. It will be appreciated that the shaft 130 could have a circular cross section, a polygonal cross section, a rectangular cross section, a cruciform cross section, or any other shaft cross section known to persons having skill in the art.

The radial projection 106 may include an axisymmetric surface of revolution about a longitudinal axis 146 of the shaft, where the radial projection 106 either partially or completely surrounds the shaft 130 in a circumferential direction 170 about the shaft 130. Alternatively, the radial projection 106 may include any other structure defining a cross section in a plane including the radial direction 126 and the axial direction 128, where the structure projects from the shaft 130 at least partly in the radial direction 126. According to an aspect of the disclosure, the radial projection 106 is fixed to the shaft 130, such that the radial projection 106 is not free to translate relative to the shaft 130 along a longitudinal axis 146 of the shaft 130, and the radial projection 106 is not free to rotate relative to the shaft 130 about the longitudinal axis 146.

The at least one radial projection 106 may include an axial array of radial projections including two or more radial projections 106 disposed at different axial locations along the shaft 130 relative to the axial direction 128. Two or more radial projections 106 of the axial array may be located at substantially identical circumferential locations about the shaft 130.

The at least one radial projection 106 may include a circumferential array of radial projections 106 disposed at different circumferential locations about the longitudinal axis 146 of the plunger 104. Two or more radial projections 106 of the circumferential array may be located at substantially identical axial locations along the shaft 130 relative to the axial direction 128.

Figure 2:
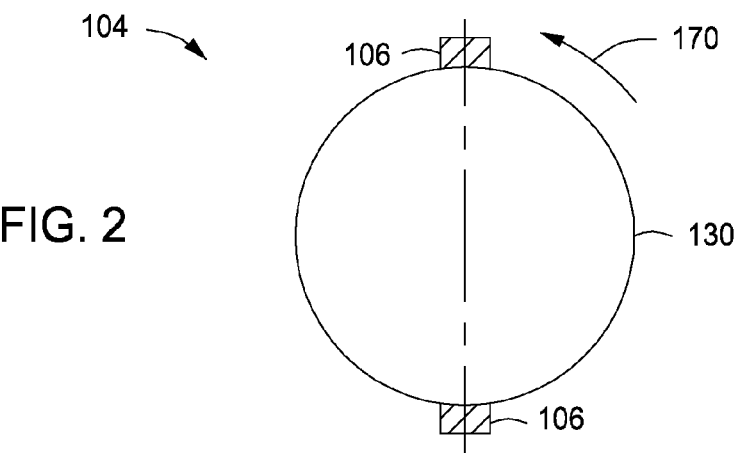
FIGS. 2-4 are radial cross sectional views of plungers, according to various aspects of the disclosure.
Figure 3:
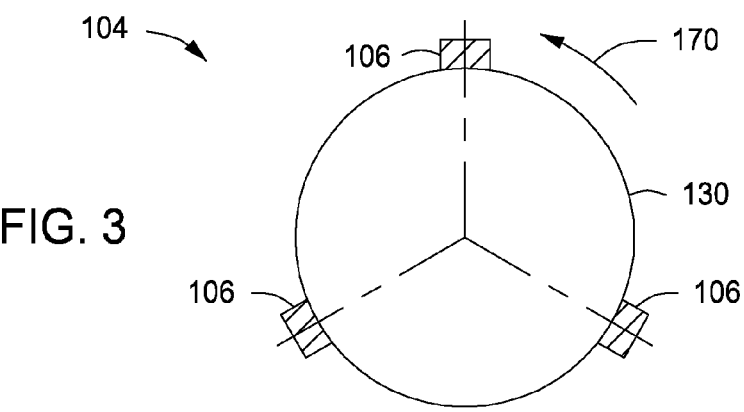
Figure 4:
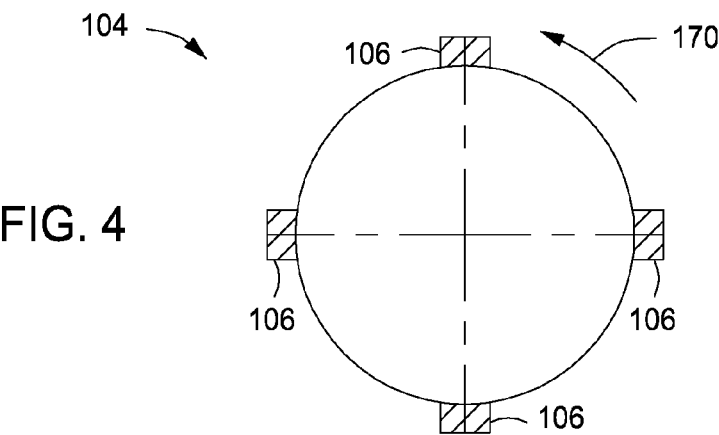

Referring now to FIGS. 2-4, it will be appreciated that FIG. 2 shows a radial cross section of a plunger 104, according to an aspect of the disclosure; FIG. 3 shows a radial cross section of a plunger 104, according to an aspect of the disclosure; and FIG. 4 shows a radial cross section of a plunger 104, according to an aspect of the disclosure.

As shown in FIG. 2, the two or more radial projections 106 may be arranged in a circumferential array about the shaft 130, such that one of the two or more radial projections 106 is disposed substantially opposite the other of the two or more radial projections 106 in the circumferential direction 170.

As shown in FIG. 3, the two or more radial projections 106 may include three radial projections 106 arranged at different circumferential locations about the shaft 130 in the circumferential direction 170. According to an aspect of the disclosure, the three radial projections 106 may be disposed in a substantially uniform array in the circumferential direction 170. According to another aspect of the disclosure, the three radial projections 106 may all be disposed at substantially the same axial location along the shaft 130.

As shown in FIG. 4, the two or more radial projections 106 may include four radial projections 106 arranged at different circumferential locations about the shaft 130 in the circumferential direction 170. According to an aspect of the disclosure, the four radial projections 106 may be disposed in a substantially uniform array in the circumferential direction 170. According to another aspect of the disclosure, the four radial projections 106 may all be disposed at substantially the same axial location along the shaft 130.

Returning to FIG. 1, the plunger 104 is configured to translate within the bore 114 of the barrel 102 along the axial direction 128. Further, the piston 136 is configured for sliding and sealing engagement with the internal surface 108 of the barrel 102. According to one aspect of the disclosure, the longitudinal axis 120 of the barrel 102 is substantially coaxial with the longitudinal axis 146 of the plunger 104. However, it will be appreciated that the longitudinal axis 120 of the barrel 102 need not be substantially coaxial with the longitudinal axis 146 of the plunger 104.

Translation of the piston 136 away from the first aperture 110 along the axial direction 128 may act to draw material from outside the barrel 102 into the internal bore 114 of the barrel 102 via the first aperture 110. Conversely, translation of the piston 136 toward the first aperture 110 along the axial direction 128 may act to expel material out of the internal bore 114 of the barrel 102 via the first aperture 110.

The internal surface 108 of the barrel 102 defines an aperture 150 near the proximal end 122 having a bore 114 radial dimension 152 from the longitudinal axis 120 to the portion of the internal surface 108 defining the aperture 150. According to an aspect of the disclosure, the radial dimension 152 is the smallest radial dimension of the bore 114 between the axial location of the piston 136 within the bore 114 and the proximal end 122 of the barrel. According to another aspect of the disclosure, the aperture 150 is located at the same axial location of the aperture 112. According to another aspect of the disclosure, the aperture 150 is defined by an undercut 151 projecting radially toward the longitudinal axis 120 of the barrel.

The radial dimension 152 may be smaller than a radial dimension 154 from the longitudinal axis 146 of the plunger 104 to an outer surface of the piston 136. Further, the radial dimension 152 may be smaller than a radial dimension 156, measured from the longitudinal axis 120 of the barrel to a portion of the internal surface 108 of the barrel 102 disposed between the piston 136 and the aperture 110 in the axial direction 128.

The at least one radial projection 106 is configured to effect non-uniform resistance or force in opposition to motion of the plunger 104 relative to the barrel 102 through variation in radial interference between the outer surface of the plunger 104 and the internal surface 108 of the barrel at the minimum proximal aperture 150. According to an aspect of the disclosure, a portion of the plunger shaft 130 may have a radial dimension 160, extending from the longitudinal axis 146 of the plunger 104 to an outer surface of the shaft 130, that is less than or equal to the radial dimension 152 of the barrel aperture 150, such that there is little or no contact between the plunger shaft 130 and the internal surface 108 of the barrel at the aperture 150 when the piston 136 is disposed within the bore 114. According to another aspect of the disclosure, a radial dimension 162 from the longitudinal axis 146 of the plunger 104 to an external surface of a radial projection 106 may be greater than the radial dimension 152 of the barrel aperture 150, such that radial interference between the radial projection 106 and the internal surface 108 at the aperture 150 effects increased resistance to translating the plunger 104 relative to the barrel 102. Thus, the radial profile of the plunger 104 may provide haptic feedback to a user of the syringe 100 that is indicative of a location of the plunger 104 relative to the barrel 102 in the axial direction 128.

Sliding contact between an outer surface of a radial projection 106 and the internal surface 108 of the barrel at the aperture 150 may cause elastic deformation of the radial projection 106, plastic deformation of the radial projection 106, elastic deformation of the internal surface 108 of the barrel, plastic deformation of the internal surface 108 of the barrel, or combinations thereof. According to an aspect of the disclosure, an entire axial length 164 of a radial projection 106 may traverse the aperture 150 by translating the plunger 104 relative to the barrel 102 without breaking any portion of the radial projection 106 away from the plunger 104. Accordingly, the at least one radial projection 106 may not be frangible relative to the plunger 104 by operation of the plunger 104 within the barrel 102.

Figure 5:
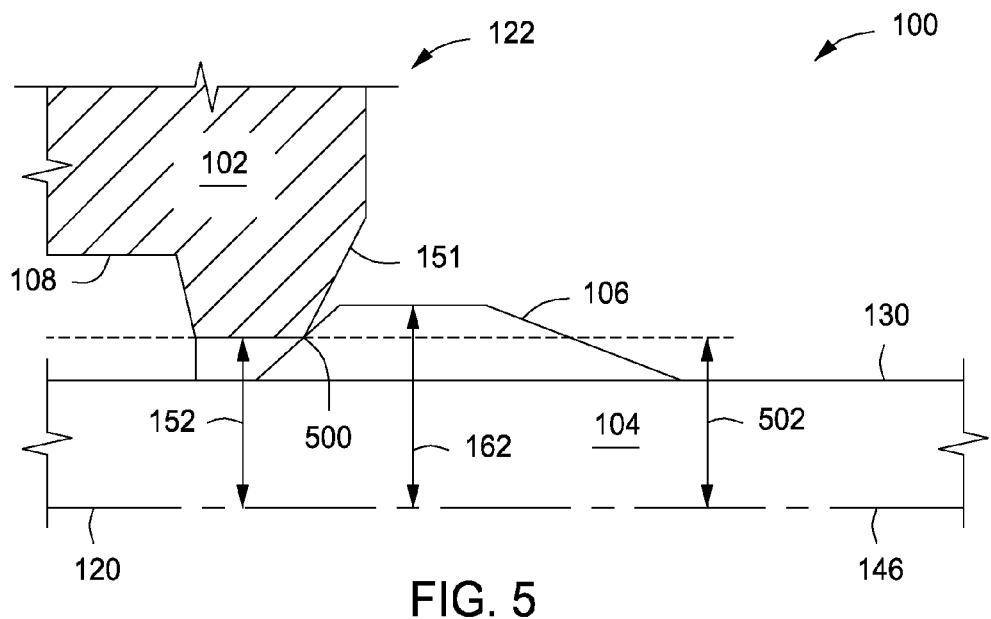
FIGS. 5 and 6 are partial cross sectional views of syringes, according to various aspects of the disclosure.
Figure 6:
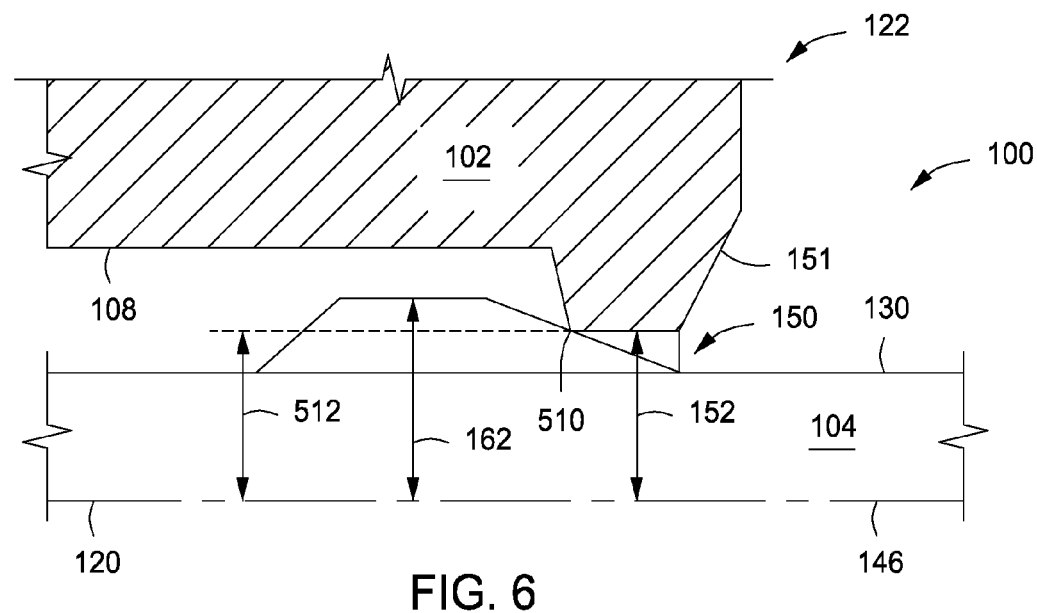

Referring to FIGS. 5 and 6, it will be appreciated that FIG. 5 shows a partial cross sectional view of the syringe 100, according to an aspect of the disclosure; and FIG. 6 shows a partial cross section view of the syringe 100, according to an aspect of the disclosure. As shown in FIG. 5, the plunger 104 may be translated toward the barrel 102 until the radial projection 106 contacts the barrel 102 at a leading incipient point of contact 500, such that the leading incipient point of contact 500 is spaced apart from the longitudinal axis 146 of the plunger 104, the longitudinal axis 120 of the barrel 102, or both, by a radial distance 502.

As shown in FIG. 6, the plunger 104 may be translated toward the barrel until the radial projection 106 contacts the barrel 102 at a trailing incipient point of contact 510, such that the trailing incipient point of contact 510 is spaced apart from the longitudinal axis 146 of the plunger 104, the longitudinal axis 120 of the barrel 102, or both, by a radial distance 512. It will be appreciated that the radial distance 512 (see FIG. 6) may or may not be equal to the radial distance 502 (see FIG. 5) depending on the profile of the internal surface 108 of the barrel 102 defining the undercut 151.

Figure 7:
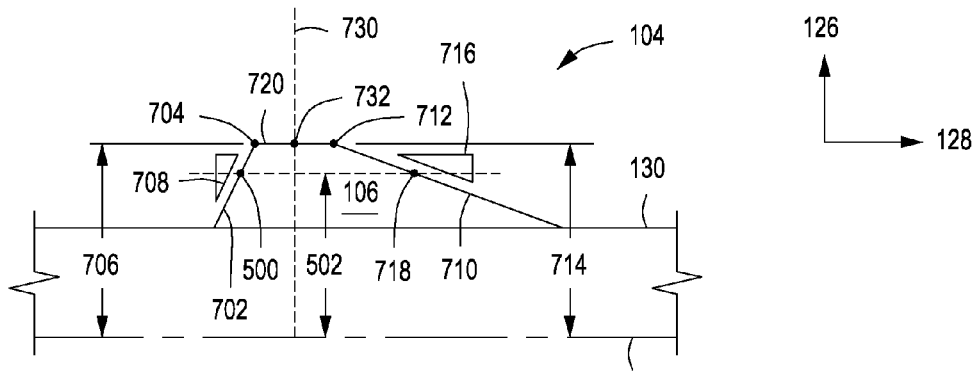
FIGS. 7-11 are schematic views of radial projections for a plunger, according to various aspects of the disclosure.

FIGS. 7-11 show axial cross sectional views of the plunger 104, according to various aspects of the disclosure. As shown in FIG. 7, the plunger 104 includes a radial projection 106 having a distal ramp 702 extending from the external surface of the shaft 130 to a point of maximum radial height 704. The point of maximum radial height 704 of the distal ramp 702 is located a radial distance 706 from the longitudinal axis 146. The distal ramp 702 has a slope 708, with respect to the radial direction 126 and the axial direction 128, at its point of leading incipient contact 500 with the barrel 102.

The radial projection 106 also includes a proximal ramp 710 extending from the external surface of the shaft 130 to a point of maximum radial height 712. The point of maximum radial height 712 of the proximal ramp 710 is located a radial distance 714 from the longitudinal axis 146. The proximal ramp 710 has a slope 716, with respect to the radial direction 126 and the axial direction 128, at a point 718 located at the radial distance 502 from the longitudinal axis 146.

It will be appreciated that the radial distance 706 to the point of maximum radial height 704 for the distal ramp 702 may or may not be equal to the radial distance 714 to the point of maximum radial height 712 for the proximal ramp 710. According to an aspect of the disclosure, the point of maximum radial height 704 for the distal ramp 702 may be separated from the point of maximum radial height 712 for the proximal ramp in the axial direction 128 by a plateau surface 720. According to another aspect of the disclosure, the point of radial height 704 for the distal ramp 702 may be coincident with the point of radial height 712 for the proximal ramp 710, such that there is no plateau surface 720 therebetween.

It will be appreciated that the distal ramp 702 may be distinguished from the proximal ramp 710 or the plateau surface 720 by a discontinuity in slope therebetween. Further, it will be appreciated that such discontinuities in slope may be discerned by persons having skill in the art notwithstanding smoothed or radiused corners transitioning from either the distal ramp 702 or the proximal ramp 710 to an adjacent surface on the radial projection 106.

According to an aspect of the disclosure, the absolute value of the slope 708 of the distal ramp 702 does not equal the absolute value of the slope 716 of the proximal ramp 710. According to another aspect of the disclosure, the absolute value of the slope 708 of the distal ramp 702 is greater than the absolute value of the slope 716 of the proximal ramp 710. For example, the absolute value of the slope 708 of the distal ramp 702 may be greater than 45 degrees and the absolute value of the slope 716 of the proximal ramp 710 may be less than 45 degrees. According to yet another aspect of the disclosure, the absolute value of the slope 708 of the distal ramp 702 is less than the absolute value of the slope 716 of the proximal ramp 710.

It will be appreciated that the distal ramp 702 and the proximal ramp 710 may include linear profiles in the plane defined by the radial direction 126 and the axial direction 128, such that the slope 708 of the distal ramp 702 lies on a linear profile of the distal ramp 702, and such that the slope 716 of the proximal ramp lies on a linear profile of the proximal ramp 710.

According to an aspect of the disclosure, profiles of the distal ramp 702 and the proximal ramp 710 may be non-symmetric about a plane 730 normal to the longitudinal axis 146 and located at a point 732 halfway between the points of maximum radial height 704 and 712 in the axial direction 128. According to another aspect of the disclosure, the points of maximum radial height 704 and 712 are coincident, and the plane 730 passes through the points of maximum radial height 704 and 712.

Figure 8:
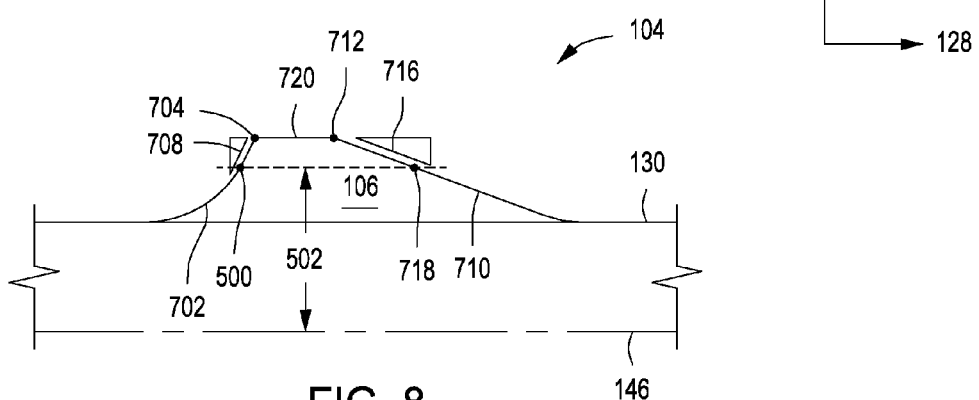
Figure 9:
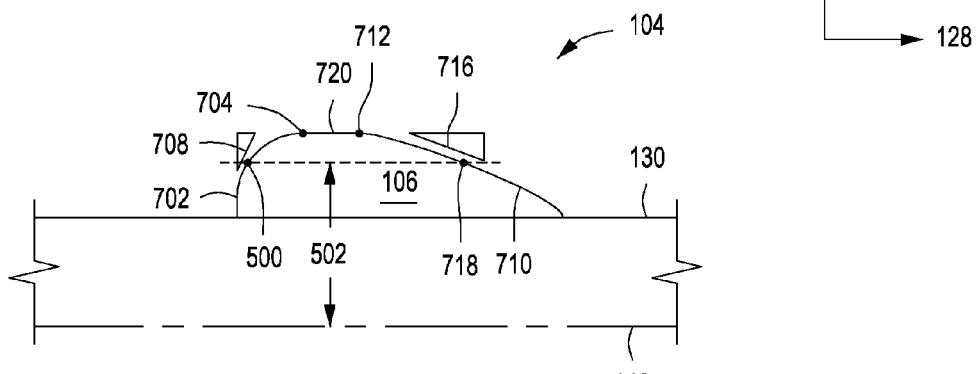
Figure 10:
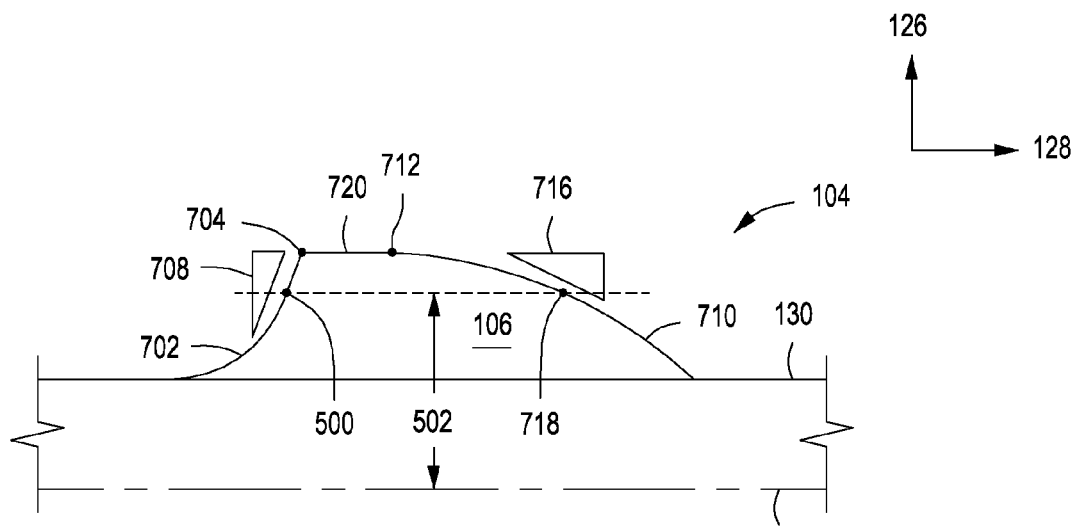

As shown in FIG. 8, either the distal ramp 702 or the proximal ramp 710 may include concave profiles in the plane defined by the radial direction 126 and the axial direction 128. As shown in FIG. 9, either the distal ramp 702 or the proximal ramp 710 may include convex profiles in the plane defined by the radial direction 126 and the axial direction 128. As shown in FIG. 10, the distal ramp 702 may include a concave profile and the proximal ramp 710 may include a convex profile, both with respect to the plane defined by the radial direction 126 and the axial direction 128. Conversely, it will be appreciated that the proximal ramp 710 may include a convex profile and the proximal ramp 710 may include a concave profile.

Figure 11:
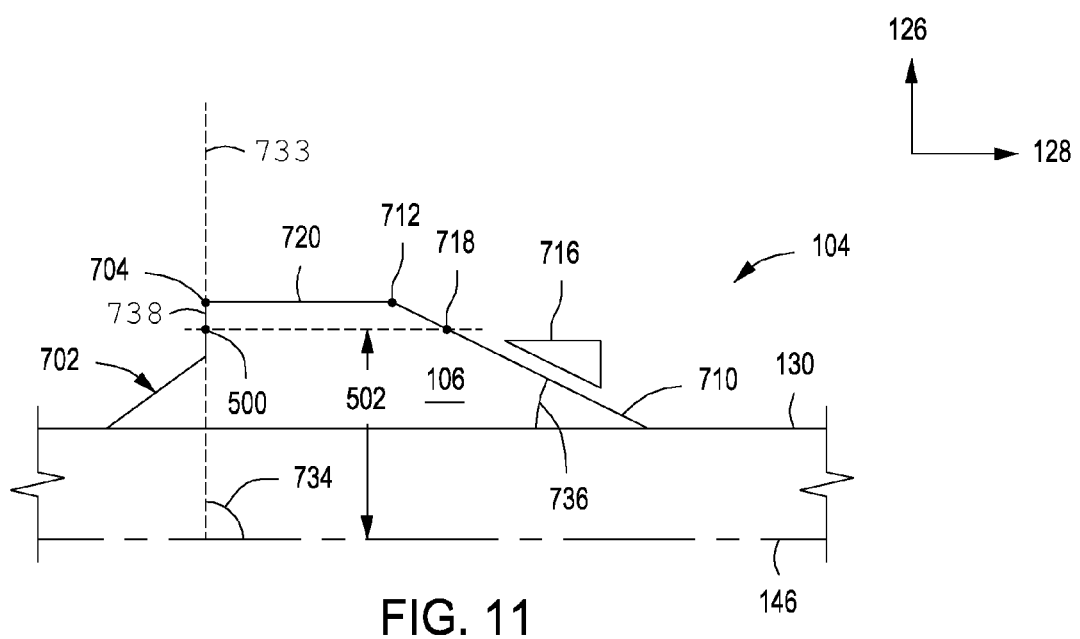

As shown in FIG. 11, the distal ramp 702 may include an abutment surface 738, where the abutment surface 738 defines the point of leading incipient contact 500 with the inner surface 108 of the barrel 102 (see FIG. 5). The abutment surface 738 may have a linear profile, a concave profile, or a convex profile. According to an aspect of the disclosure, a line 733 tangent to the abutment surface 738 at the point of leading incipient contact 500 forms an angle 734 with the longitudinal axis 146 of approximately 90 degrees. According to another aspect of the disclosure, no line tangent to the proximal ramp 710 forms an angle 736 with the longitudinal axis 146 of approximately 90 degrees. Here, approximately 90 degrees will be understood to be an angle between about 80 degrees and about 100 degrees.

The present disclosure is applicable to syringes in general, and more particularly, to syringes that provide haptic or tactile feedback of material quantity delivered to the user. Further, the present disclosure may be applicable to syringes used in the context of medicine, manufacturing, construction, maintenance and repair, agriculture, food preparation, or any other context where syringes may be used. Accordingly, aspects of the disclosure may be applied to syringes for delivering a medication to a patient, extracting bodily fluids from a patient, or delivering other fluid materials such as air, adhesives, lubricants, food products, and the like.

Operation of the syringe 100 will now be described with reference to FIG. 1. The plunger 104 translates within the bore 114 of the barrel 102 toward the port 110 with a relatively low resistance until the at least one radial projection 106 contacts the internal surface 108 of the barrel 102 at the leading point of incipient contact 500 (see FIG. 5). After incipient contact between the radial projection 106 of the plunger 104 and the barrel 102, the increased resistance provides haptic feedback to a user indicating an axial position of the plunger 104 relative to the barrel 102.

According to an aspect of the disclosure, the location of the at least one radial projection 106 along the axial length of the plunger 104 corresponds to a stopping point against the barrel 102 for a swept piston 136 volume within the bore 144 for a desired dose of material discharged from the syringe 100. Accordingly, the syringe 100 user may stop translation of the plunger 104 into the barrel 102 upon sensation of the haptic feedback caused by incipient contact between the at least one radial projection 106 and the internal surface 108 of the barrel 102.

Next, the user may then proceed to deliver a second dose of material from the syringe 100 by applying sufficient force to translate the plunger 104 against the interference between the at least one radial projection 106 and the inner surface 108 of the barrel 102. When the proximal ramp of the radial projection 106 is in trailing incipient contact with the inner surface 108 of the barrel 102, the user may feel reduced resistance to further translation of the plunger 104 into the barrel 102, and may continue to translate the plunger 104 into the barrel 102 until a second increase in plunger resistance is perceived. The second increase in plunger resistance may be the result of incipient contact between a distal ramp of a subsequent radial projection 106, or a hard stop such as abutting contact between the piston 136 and the internal surface 108 of the barrel, or any other abutting contact between the plunger 104 and the barrel 102.

According to aspects of the disclosure, asymmetry between the distal and proximal ramps of the radial projections 106 allow designers to further refine the haptic or tactile feedback by tailoring the relative resistances of leading incipient contact and trailing incipient contact between the at least one radial projection 106 and the internal surface 108 of the barrel 102. For example, the slope of the distal ramp may be steeper than the slope of the proximal ramp, thereby effecting more abrupt deceleration of the plunger 104 relative to the barrel 102 upon delivering a dose, and more gradual acceleration of the plunger 104 relative to the barrel 102 upon the beginning of delivering a subsequent dose of material from the syringe 100.

Thus, aspects of the present disclosure provide apparatus and methods for indicating an axial position of a plunger 104 within a barrel 102 of a syringe 100 through haptic feedback via variable resistance or force for motion of the plunger 104 relative to the barrel 102. Accordingly, a user may deliver multiple doses of material from the syringe 100 without needing to visually observe the location of the plunger 104 relative to the barrel 102, and potentially while operating the syringe 100 with just one hand, thereby freeing up the user's other hand to perform other operations in parallel with delivering material from the syringe 100.

Applicants have identified a need for delivering multiple doses of medication from a single syringe using rapid plunger motion to deliver each of the multiple doses. For example, nasal administration of medications may benefit from delivery of partial doses to each nostril of a patient in quick succession and with a high degree of atomization.

The degree of atomization increases with increasing pressure drop across the atomization orifice, and therefore, increasing flow rate through the atomization orifice. Accordingly, the degree of atomization may benefit from higher velocities of the plunger 104 relative to the barrel 102 during medicine delivery. In turn, Applicants have identified that high plunger velocities for multi-dose syringes may result in repeatability and reproducibility errors, in both the amount of medicine in each dose and the degree of atomization, when dose quantity is controlled via visual feedback of a relative position of the plunger 104 within the barrel 102 of the syringe. Indeed, errors in dose quantity based on visual feedback may be exacerbated by the need for high plunger velocities at least because of difficulty in rapidly decelerating the plunger 104 to while simultaneously stopping precisely at the axial location corresponding to a desired dose.

Aspects of the disclosure address drawbacks of conventional approaches by providing tactile dose feedback through variable interference between the plunger 104 and the barrel 102 of a syringe, instead of conventional visual feedback. As described previously, variable interference between a plunger 104 and a barrel 102 of a syringe 100 may be varied according to aspects of the disclosure to provide variable degrees of tactile interference indicative of the position of the plunger 104 within the barrel 102. Indeed, by providing tactile feedback indicative of individual dose quantities, syringe users may allocate more attention to the rate of plunger travel and the location of the aperture 110 relative to a patient's nose, for example, thereby improving repeatability and reproducibility of both dose quantity and the degree of atomization.

In addition, aspects of the disclosure provide a dose dividing syringe 100 that allows translation of the plunger 104 away from the barrel 102, for example during filling procedures. Unlike conventional multiple-dose syringes, such as those described in the '544 patent and the '467 publication, discussed above, syringes according to the present disclosure may not require rotation of the plunger shaft 130 in order to fill the syringes with material.

The syringe 100 may be configured with an axial array of radial projections 106 such that a first dose of material, corresponding to translation of the plunger 104 until contact between a first radial projection 106 and the barrel 102, may be substantially equal in quantity to a second dose of material, corresponding to translation of the plunger 104 until contact between a second radial projection 106 and the barrel 102 of the syringe 100. However, it will be appreciated that the syringe 100 may also be configured such that the quantity of the first dose of material is different from the quantity of the second dose of material for other material delivery processes.

Unless specified otherwise herein, the word "substantially" shall mean "considerable in extent," or shall mean largely but not necessarily wholly that which is specified.

It will be appreciated that the foregoing description provides examples of the disclosed apparatus and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

We claim:
1. A syringe, comprising:
  a barrel having an internal surface defining an internal bore therein;
  a plunger disposed within the internal bore of the barrel, a distal end of the plunger being inserted into a proximal end of the barrel, a proximal end of the plunger being opposite the distal end of the plunger along a longitudinal axis of the plunger; and at least one radial projection disposed on an external surface of the plunger, the at least one radial projection including a proximal ramp and a distal ramp, the proximal ramp being disposed on a proximal side of the at least one radial projection, and the distal ramp being disposed on a distal side of the at least one radial projection, the distal ramp having a first maximum radial height from the longitudinal axis, and the proximal ramp having a second maximum radial height from the longitudinal axis, the distal ramp including a leading point of incipient contact with the internal surface of the barrel, the first leading point of incipient contact being located at a first radial distance from the longitudinal axis, the at least one radial projection having a first slope relative to the longitudinal axis at the leading point of incipient contact, the at least one radial projection having a second slope at a trailing point of contact with the internal surface of the barrel along the proximal ramp located a second radial distance from the from the longitudinal axis, the second radial distance being substantially equal to the first radial distance, and an absolute value of the first slope being different from an absolute value of the second slope, wherein the first slope at the leading point of incipient contact on the distal ramp is a continuous slope, and wherein the first radial distance of the leading point of incipient contact on the distal ramp is less than a maximum radial height of the distal ramp, and wherein the second slope at the trailing point of contact on the proximal ramp is a continuous slope, and wherein the second radial distance of the trailing point of contact on the proximal ramp is less than a maximum radial height of the proximal ramp.

2. The syringe according to claim 1, wherein the internal bore of the barrel includes an undercut near a proximal end of the barrel, the undercut defining a minimum inscribed diameter of the internal bore, and a maximum circumscribed diameter of the plunger at the at least one radial projection is greater than the minimum inscribed diameter of the internal bore.

3. The syringe according to claim 1, wherein the at least one radial projection consists of a plurality of radial projections.

4. The syringe according to claim 1, wherein the at least one radial projection includes at least two radial projections located at substantially identical axial locations along the longitudinal axis.

5. The syringe according to claim 1, wherein the at least one radial projection includes at least two radial projections located at substantially identical circumferential locations about the plunger.

6. The syringe according to claim 1, wherein the absolute value of the first slope is greater than the absolute value of the second slope.

7. The syringe according to claim 1, wherein the first slope is perpendicular to the longitudinal axis.

8. The syringe according to claim 1, wherein the second slope is not perpendicular to the longitudinal axis.

9. The syringe according to claim 1, wherein the proximal ramp includes a first substantially linear ramp.

10. The syringe according to claim 9, wherein the distal ramp includes a second substantially linear ramp.

11. The syringe according to claim 9, wherein the distal ramp includes a convex ramp.

12. The syringe according to claim 9, wherein the distal ramp includes a concave ramp.

13. The syringe according to claim 1, wherein the proximal ramp includes a first convex ramp.

14. The syringe according to claim 1, wherein the proximal ramp includes a first concave ramp.

\* \* \* \* \*